(12) United States Patent  (10) Patent No.: US 8,218,723 B2
Ein-Gal  (45) Date of Patent: Jul. 10, 2012

(54) SUPPORT SYSTEM FOR BREAST IRRADIATION

(76) Inventor: Moshe Ein-Gal, Ramat Hasharon (IL)

( * ) Notice: Subject to any disclaimer, the term of this patent is extended or adjusted under 35 U.S.C. 154(b) by 0 days.

(21) Appl. No.: 12/501,437

(22) Filed: Jul. 12, 2009

(65) Prior Publication Data

US 2011/0007868 A1    Jan. 13, 2011

(51) Int. Cl.
*A61B 6/04*    (2006.01)
*H05G 1/02*    (2006.01)

(52) U.S. Cl. .......................................... 378/37; 378/208

(58) Field of Classification Search .................... 378/37, 378/17, 20, 204, 208, 209; 600/415; 5/600, 5/601, 611
See application file for complete search history.

(56) References Cited

U.S. PATENT DOCUMENTS

| 2,552,592 | A | * | 5/1951 | Rush | 297/195.11 |
| 5,168,514 | A | * | 12/1992 | Horton et al. | 378/209 |
| 2006/0262898 | A1 | * | 11/2006 | Partain et al. | 378/37 |
| 2007/0211854 | A1 | * | 9/2007 | Koshnitsky et al. | 378/65 |
| 2009/0054757 | A1 | * | 2/2009 | Noras | 600/415 |
| 2009/0064413 | A1 | * | 3/2009 | Sliski et al. | 5/601 |
| 2009/0080602 | A1 | * | 3/2009 | Brooks et al. | 378/20 |
| 2010/0074400 | A1 | * | 3/2010 | Sendai | 378/37 |
| 2010/0098214 | A1 | * | 4/2010 | Star-Lack et al. | 378/65 |

* cited by examiner

*Primary Examiner* — Anastasia Midkiff
(74) *Attorney, Agent, or Firm* — Dekel Patent Ltd.; David Klein

(57) ABSTRACT

A support system for breast irradiation including a turntable for supporting and rotating a patient about a generally vertical rotational axis, a body-leaning support for supporting the patient leaning thereupon throughout rotation of the patient about the vertical rotational axis, and a radiation shield arranged for shielding non-breast anatomy of the patient from stray radiation, wherein the body-leaning support and the radiation shield are separated from each other by a gap in which breasts of the patient are placeable for irradiation by a horizontal radiation beam.

16 Claims, 1 Drawing Sheet

SUPPORT SYSTEM FOR BREAST IRRADIATION

FIELD OF THE INVENTION

The present invention generally relates to radiotherapy systems, and more particularly to a support system for breast irradiation that supports the patient in a leaning position and shields the patient from unwanted radiation, e.g., radiation passing through the breast.

BACKGROUND OF THE INVENTION

In prior art systems for computerized tomography and radiotherapy of the breast, the patient is horizontally positioned, while for mammography the patient may be positioned vertically. Systems with a horizontal patient in the prone position have an advantage of reduced exposure of organs other than the breast. A disadvantage of prone or supine systems is that they are not suitable for upright radiotherapy, wherein the patient or the source rotates about a vertical rotational axis, since the required source-axis-distance (SAD) in order to prevent collision of the patient's legs with the equipment is prohibitively large. Another disadvantage of such systems is the limited angular range of irradiating beams due to: a) excluding orientations where residual radiation may expose other organs and b) difficulty in blocking the residual radiation.

SUMMARY OF THE INVENTION

The present invention seeks to provide an improved support system for breast upright radiotherapy that supports the patient in a leaning position and shields the patient from unwanted or residual radiation, as is described more in detail hereinbelow. In contrast to the prior art, the system of the invention rotates the patient about a vertical rotational axis intersecting the breast while the patient is standing, bent or reclining, such that an acceptable SAD is achieved for preventing the patient's legs from colliding with adjacent equipment. Target localization can be performed with suitable imaging equipment.

There is thus provided in accordance with an embodiment of the present invention a support system for breast irradiation including a turntable for supporting and rotating a patient about a generally vertical rotational axis, a body-leaning support for supporting the patient leaning thereupon throughout rotation of the patient about the vertical rotational axis, and a radiation shield arranged for shielding non-breast anatomy of the patient from stray radiation, wherein the body-leaning support and the radiation shield are separated from each other by a gap in which a breast of the patient is placeable for irradiation by a horizontal radiation beam.

In accordance with an embodiment of the present invention the body-leaning support and/or the radiation shield are mechanically fixed to the turntable and rotate therewith.

In accordance with an embodiment of the present invention the body-leaning support and/or the radiation shield include a tiltable support pad for the patient to rest against.

In accordance with an embodiment of the present invention the turntable is also operable to move the patient linearly.

There is also provided in accordance with an embodiment of the present invention a breast irradiation system including a radiation source operative to emit a generally horizontal radiation beam towards a breast of a patient, a turntable for supporting and rotating the patient about a generally vertical rotational axis, a body-leaning support for supporting the patient leaning thereupon throughout rotation of the patient about the vertical rotational axis, and a radiation shield arranged for shielding non-breast anatomy of the patient from stray radiation, wherein the body-leaning support and the radiation shield are separated from each other by a gap in which a breast of the patient is placeable for irradiation by the horizontal radiation beam.

In accordance with an embodiment of the present invention an imaging system is provided that can image the breast from at least two angles.

In accordance with an embodiment of the present invention a video camera is provided for monitoring the breast position during treatment.

There is also provided in accordance with an embodiment of the present invention a method for breast irradiation including supporting and rotating a patient about a generally vertical rotational axis, wherein the patient leans against and is supported by a body-leaning support throughout rotation of the patient about the vertical rotational axis, and irradiating the breast with a generally horizontal radiation beam, and shielding non-breast anatomy of the patient from stray radiation.

BRIEF DESCRIPTION OF THE DRAWINGS

The present invention will be understood and appreciated more fully from the following detailed description, taken in conjunction with the drawing in which.

DETAILED DESCRIPTION OF EMBODIMENTS

Figure 1A:
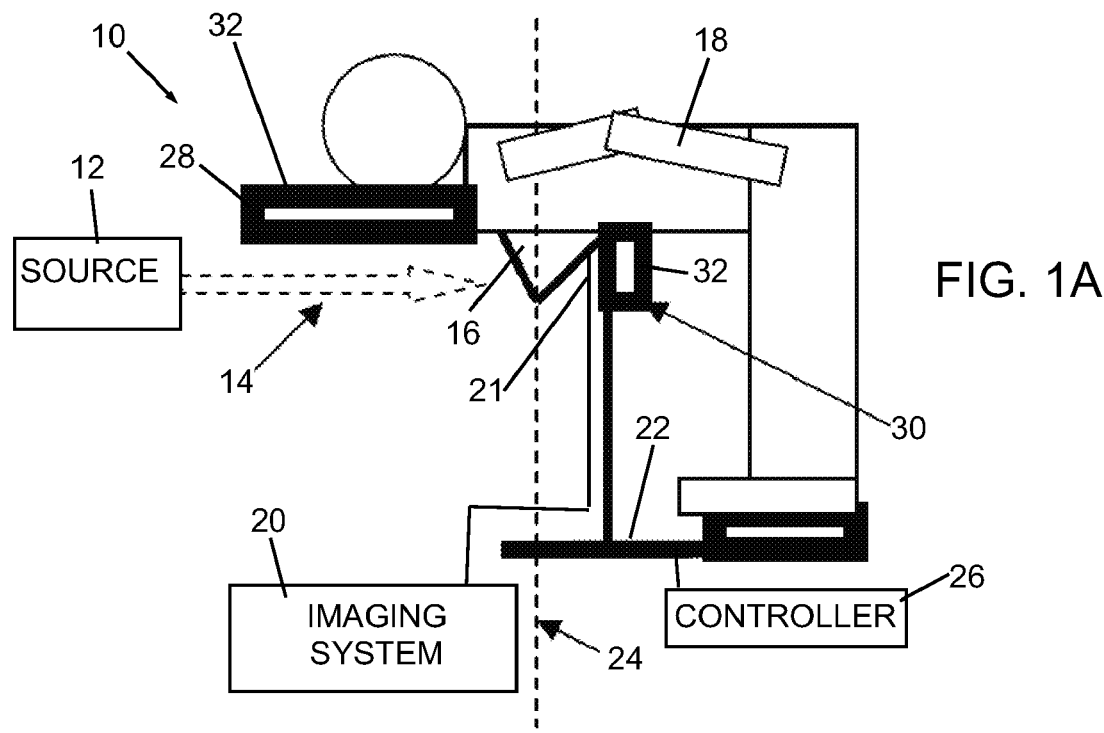
FIGS. 1A and 1B are simplified illustrations of a support system for breast irradiation, constructed and operative in accordance with an embodiment of the present invention.
Figure 1B:
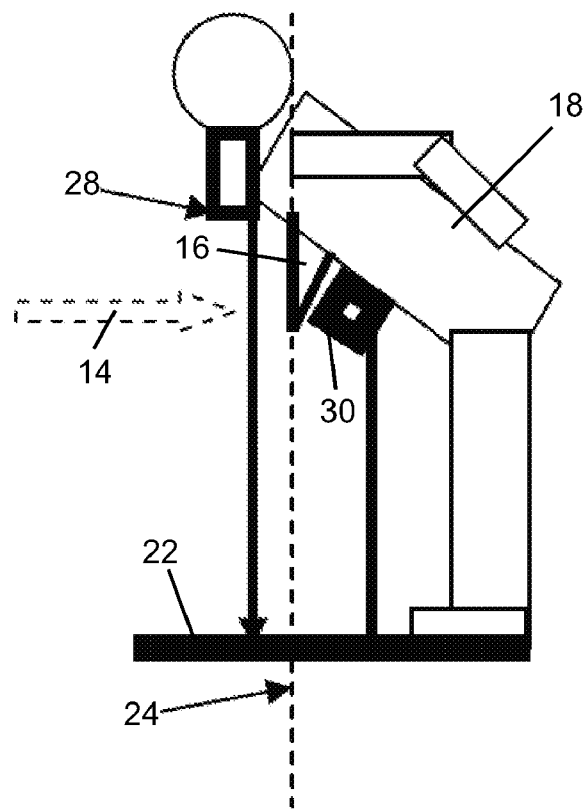

Reference is now made to FIGS. 1A and 1B, which illustrate a support system 10 for breast irradiation, constructed and operative in accordance with an embodiment of the present invention.

Support system 10 can be used in conjunction with a breast irradiation system that has a radiation source 12 that emits a generally horizontal radiation beam 14 towards a breast 16 of a patient 18. In the non-limiting illustrated embodiment, an imaging system 20 is provided that can image the breast 16 from at least two angles. Imaging system 20 includes imaging detectors 21 and other associated components well known in the art.

In the non-limiting illustrated embodiment, support system 10 includes a turntable 22 for supporting and rotating patient 18 about a generally vertical rotational axis 24. Rotation of turntable 22 is actuated and controlled by a controller 26 that can work in a feedback system in conjunction with the breast irradiation system and/or imaging system. In this manner, the patient 18 can be rotated to and stopped at a desired angle for irradiation thereat, or irradiated while being rotated at a desired rotational speed. In accordance with an embodiment of the present invention, turntable 22 is also operable to move patient 18 linearly, such as along a track or groove.

A body-leaning support 28 is provided for supporting patient 18 leaning thereupon throughout rotation about vertical rotational axis 24. A radiation shield 30, containing lead or tungsten or other shielding material, is arranged for shielding non-breast anatomy of patient 18 from stray ("stray" includes residual) radiation (e.g., the hips and legs). The body-leaning support 28 and radiation shield 30 are separated from each other by a gap in which breasts 16 are placeable for irradiation by horizontal radiation beam 14.

In accordance with an embodiment of the present invention the body-leaning support 28 and/or the radiation shield 30 are mechanically fixed to turntable 22 and rotate therewith. (For the sake of simplicity, the link between support 28 and turntable 22 in FIG. 1A is not shown.) It is noted that imaging system 20 is preferably stationary, but can optionally be fixed to turntable 22 and rotate therewith.

In accordance with an embodiment of the present invention the body-leaning support 28 and/or radiation shield 30 include a tiltable support pad 32 for patient 18 to rest against. The tiltable support pad 32 may be tilted to or positioned in a desired angle for the patient's comfort and locked in place, such as by means of a mechanical fastener (e.g., screw, pin, locknut, etc.). FIG. 1A shows the patient 18 bent over at a 90° angle, whereas FIG. 1B shows the patient 18 bent over at an acute angle, such as 45° (FIG. 1B omits some of the elements for the sake of simplicity). In all cases, the body-leaning support 28 supports patient 18 in a lean-forward position such that the patient's center of gravity is generally below the body-leaning support 28.

The scope of the present invention includes both combinations and subcombinations of the features described hereinabove as well as modifications and variations thereof which would occur to a person of skill in the art upon reading the foregoing description and which are not in the prior art.

What is claimed is:

1. A support system for breast irradiation by a horizontal radiation beam, the support system comprising:
   a turntable for supporting and rotating a patient about a generally vertical rotational axis, said turntable having a portion for the patient to stand thereupon;
   a body-leaning support for supporting the patient leaning thereupon throughout rotation of the patient about said vertical rotational axis, said body-leaning support supporting the patient in a lean-forward position such that a center of gravity of the patient is generally below said body-leaning support; and
   a radiation shield arranged for shielding non-breast anatomy of the patient from residual radiation that has passed through a breast of the patient, wherein said radiation shield comprises a radiation-shielding tiltable support pad for the patient to rest against, wherein said tiltable support pad is pivotally mounted on a vertical member that extends vertically from said turntable and axially spaced from said portion for the patient to stand thereupon.

2. The support system according to claim 1, wherein said body-leaning support is mechanically fixed to said turntable and rotates therewith.

3. The support system according to claim 1, wherein said radiation shield is mechanically fixed to said turntable and rotates therewith.

4. The support system according to claim 1, wherein said body-leaning support comprises a tiltable support pad for the patient to rest against.

5. The support system according to claim 1, wherein when the patient is resting against said body-leaning support, said tiltable support pad is under the breast and between the breast and legs of the patient.

6. The support system according to claim 1, wherein said turntable is also operable to move the patient linearly.

7. A breast irradiation system comprising:
   a radiation source operative to emit a generally horizontal radiation beam towards a breast of a patient;
   a turntable for supporting and rotating the patient about a generally vertical rotational axis, said turntable having a portion for the patient to stand thereupon;
   a body-leaning support for supporting the patient leaning thereupon throughout rotation of the patient about said vertical rotational axis, said body-leaning support supporting the patient in a lean-forward position such that a center of gravity of the patient is generally below said body-leaning support; and
   a radiation shield arranged for shielding non-breast anatomy of the patient from stray radiation, wherein said body-leaning support and said radiation shield are separated from each other by a gap in which breasts of the patient are placeable for irradiation by said horizontal radiation beam, and wherein said radiation shield comprises a radiation-shielding tiltable support pad for the patient to rest against, wherein said tiltable support pad is pivotally mounted on a vertical member that extends vertically from said turntable and axially spaced from said portion for the patient to stand thereupon.

8. The breast irradiation system according to claim 7, wherein said body-leaning support is mechanically fixed to said turntable and rotates therewith.

9. The breast irradiation system according to claim 7, wherein said radiation shield is mechanically fixed to said turntable and rotates therewith.

10. The breast irradiation system according to claim 7, wherein said body-leaning support comprises a tiltable support pad for the patient to rest against.

11. The breast irradiation system according to claim 7, wherein when the patient is resting against said body-leaning support, said tiltable support pad is under the breast and between the breast and legs of the patient.

12. The breast irradiation system according to claim 7, wherein said turntable is also operable to move the patient linearly.

13. The breast irradiation system according to claim 8, further comprising an imaging system operable to image the breast from at least two angles.

14. A method for breast irradiation comprising:
   supporting and rotating a patient about a generally vertical rotational axis, wherein the patient leans against and is supported by a body-leaning support throughout rotation of the patient about said vertical rotational axis, said body-leaning support supporting the patient in a lean-forward position such that a center of gravity of the patient is generally below said body-leaning support; and
   irradiating the breast with a generally horizontal radiation beam, and shielding non-breast anatomy of the patient from residual radiation that has passed through a breast of the patient with a radiation shield that comprises a radiation-shielding tiltable support pad for the patient to rest against, wherein said tiltable support pad is pivotally mounted on a vertical member that extends vertically from a turntable and axially spaced from a portion of said turntable for the patient to stand there upon.

15. The support system according to claim 1, wherein said body-leaning support and said radiation shield are separated from each other by a gap in which breasts of the patient are placeable for irradiation by the horizontal radiation beam.

16. The method according to claim 14, comprising placing said tiltable support pad under the breast and between the breast and legs of the patient.

* * * * *